Figure 1:
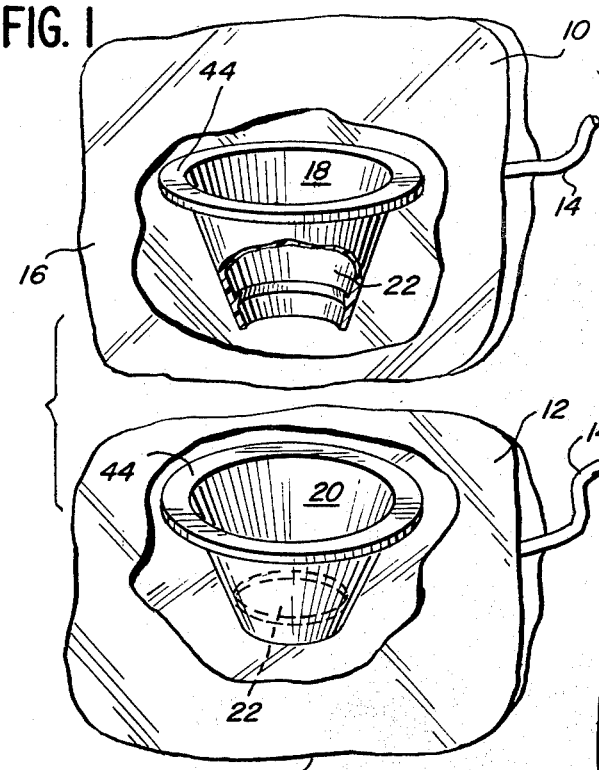

United States Patent [19]

Williams

[11] 4,253,500
[45] Mar. 3, 1981

[54] STERILE CONNECTOR ADAPTED FOR MULTIPLE JUNCTIONS

[75] Inventor: Ronald A. Williams, Mundelein, Ill.

[73] Assignee: Baxter Travenol Laboratories, Inc., Deerfield, Ill.

[21] Appl. No.: 61,214

[22] Filed: Jul. 27, 1979

[51] Int. Cl.³ .......................... B65B 3/04; B65B 3/18
[52] U.S. Cl. .......................................... 141/1; 53/468; 141/10; 141/98; 141/311 R; 156/272; 156/293; 285/4; 285/21; 285/332
[58] Field of Search .................. 53/468; 93/35 PC; 141/1, 10, 11, 82, 85, 98, 311 R, 313–317, 383, 392, 114; 156/272, 293, 294; 229/62.5; 222/541; 285/4, 21, 332

[56] References Cited

U.S. PATENT DOCUMENTS

| | | | |
|---|---|---|---|
| 4,022,256 | 5/1977 | Berkman et al. | 141/1 |
| 4,157,723 | 6/1979 | Granzow et al. | 141/1 |

*Primary Examiner*—Frederick R. Schmidt
*Attorney, Agent, or Firm*—Paul Flattery; John A. Caruso; Garrettson Ellis

[57] ABSTRACT

A sealed, sterile connection may be provided between a pair or more of containers having transparent, flexible, thermoplastic sealed walls, each of which contains an opaque, relatively rigid, hollow sealing member in the general shape of a truncated cone, open at both ends. The containers are brought together into facing contact, and the hollow sealing members are nested together with portions of the transparent walls of the containers positioned therebetween. The nested, sealing member cones are irradiated with infrared or the like through the transparent container walls to heat the nested sealing members. As a result of this, heat is conducted to the portions of the transparent walls between the nested sealing members, to seal the portions of the transparent walls together in an annular area between the sealing means. A portion of the transparent walls retained in the nested sealing members may then be torn away to make a sterile connection between the two containers.

18 Claims, 3 Drawing Figures

STERILE CONNECTOR ADAPTED FOR MULTIPLE JUNCTIONS

BACKGROUND OF THE INVENTION

In U.S. patent application Ser. No. 843,608, filed Oct. 19, 1977, now U.S. Pat. No. 4,157,723, issued June 12, 1979. and U.S. patent application Ser. No. 005,749, filed Jan. 23, 1979, among other cases, a sterile connection device between sealed conduits is shown. Each conduit can carry an opaque, thermoplastic wall portion, carried on the conduit by transparent wall portions of the conduit. The opaque wall portions of the conduits are brought together into facing contact, and then exposed to sufficient radiant energy to cause the opaque wall portions to fuse together to open an aperture through the fused wall portions, to provide sealed communication between the conduit interiors.

In accordance with this invention, a modification of the above is provided having, as a significant advantage, the possibility of placing together an unlimited number of containers or conduits at the same connection site. Opaque connection members are brought together, but do not in themselves melt. Rather, they absorb heat to form a heat seal by conduction between thermoplastic walls of the respective containers.

DESCRIPTION OF THE INVENTION

In accordance with this invention, a method and apparatus are provided for sealed, sterile connection between a pair of containers having transparent, flexible, thermoplastic, sealed walls. Each of the containers contains an opaque, relatively rigid, hollow sealing member which may be made of aluminum, for example, or another metal or high-melting plastic material.

The hollow sealing member may preferably be of the general shape of a truncated cone, open at both ends, and preferably defines annular ridge means on at least one surface thereof for forming a tear line in the sealed container walls.

Accordingly, a pair of identical flexible, transparent containers, each containing the relatively rigid, hollow sealing member, can be brought together for sterile, sealed connection by bringing the containers together into facing contact, followed by nesting the hollow sealing members together with portions of the transparent walls of the containers positioned therebetween. In this position, the transparent walls of the container are positioned to block fluid flow through the hollow nested sealing members.

Annular ridge means are positioned on the wall of a sealing member to press against the transparent wall portions to form the annular tear line of weakness, to permit opening of the flow passage through the nested sealing members by removal of the sealed bag walls from its flow-blocking position.

The nested sealing members are irradiated through the transparent container walls, to heat the nested sealing members. The heat is accordingly conducted to the portions of the transparent walls between the nested sealing members, to cause sealing of the portions of transparent sealing walls together in at least one annular area between the sealing members. As a result of this, a seal is formed between the walls of the pair of containers, and heat-sterilization may take place.

Following this, the portion of the transparent walls between the nesting sealing members may be severed, along the tear line formed by the annular ridge means, preferably with the newly-formed seal of the container walls, with all original exterior surfaces of the containers being sealed and prevented from exposure to the container interiors. The severed portion of the transparent container walls may then be removed from its flow-blocking relation with the hollow nested sealing members, to open communication between the two containers.

Preferably, the severing line is formed in the midst of the annular seal so that the severing line divides the annular seal into two annular sections. This assures the continued seal of two containers, while permitting opening of the aperture through the nested sealing member cones, maintaining the seal from the exterior of the containers, and preventing any exterior portions of a container wall from being exposed to the container interiors. Thus, the sterile or aseptic field within the container interiors is maintained.

Preferably, the majority of the area of the portions of transparent walls positioned between the nested sealing members are sealed together with the severing of the sealed area taking place between the ends of the sealed portion in the vicinity of the narrow ends of the truncated, nested sealing members, following the irradiation step to seal portions of the bag walls together between the nested sealing members.

After this, the portion of bag walls that blocks flow through the sealing members may be removed by the tearing away from the narrow end of the cone, either manually as shown below or by means of pressurizing the interior of the container adjacent the large end of the cone, so as to sever and blow out the portion through the narrow end.

Referring to the drawings, FIG. 1 is a plan view with portions broken away of a pair of containers in accordance with this invention, having transparent, flexible, thermoplastic, sealed walls, each of which contains an opaque, relatively rigid, hollow sealing member in the general shape of a truncated cone.

Figure 2:
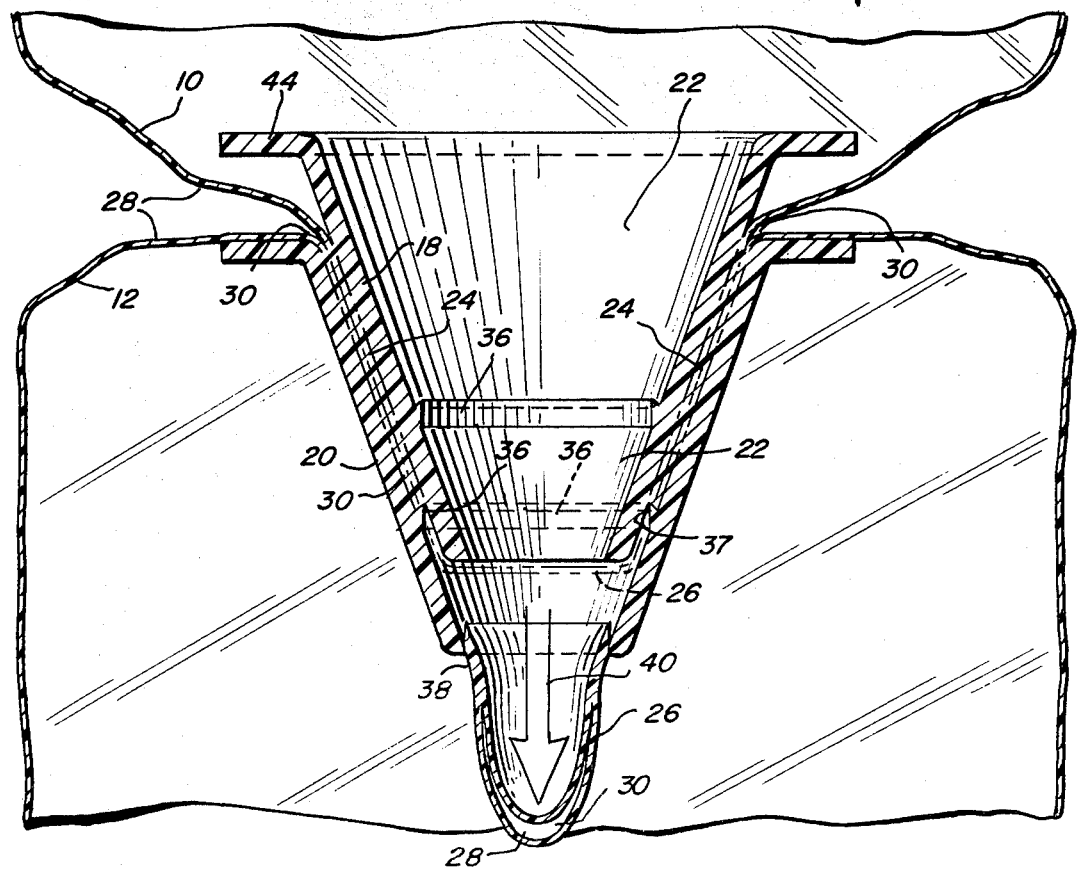

FIG. 2 is an enlarged, longitudinal sectional view of the two containers of FIG. 1 being brought together into facing contact, with the hollow sealing members being nested together with portions of the transparent walls of the container positioned therebetween, and showing one embodiment of how the flow-obstructing portions of the container walls may be removed.

Figure 3:
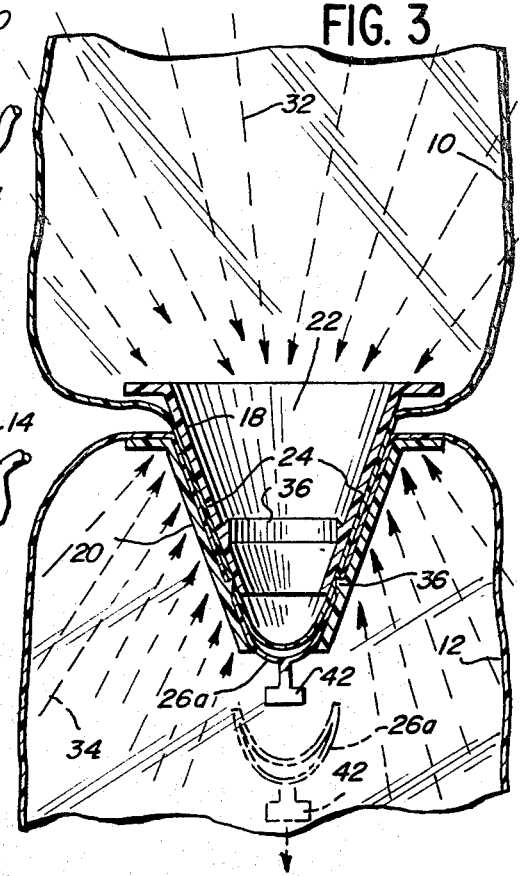

FIG. 3 is a longitudinal sectional view of the containers of FIG. 1 after they have been brought together into facing contact with the hollow sealing members nested together with portions of the transparent walls of the containers positioned therebetween, showing the structure being irradiated by infrared radiation or the like, and showing another means by which the flow obstructing portion of the sealed container walls may be removed.

Referring to the drawings, FIG. 1 shows a pair of flexible containers 10, 12 which may be conventionally made out of polyvinyl chloride plastic if desired, or any other flexible, thermoplastic material such as polyester, polyethylene, polypropylene, or copolymers thereof. Similarly, block copolymers of polystyrene and polyolefin blocks can also be used, alone or in conjunction with other ingredients, for the thermoplastic bag wall material.

Each of bags 10, 12 define one or more access tubes 14 for communication with the containers 10, 12. For example, containers 10, 12, may communicate through access tubings 14 with a single or multiple blood bag system in sterile manner, to provide the blood bag system with a versatile sterile connection means, so that the contents of the blood bag system of container 10 may be processed in any desired manner by sterile connection to one or more systems with which container 12 communicates.

Alternatively, this invention may be used in other aspects of the medical field, or the field of biochemistry and other disciplines, for either retaining materials in sterile form, or providing safe connection for highly toxic materials, living pathogenic bacteria, radioactive materials or the like.

Each of bags 10, 12 may be conventionally heat sealed about their peripheries 16 or may be blow-molded out of a tubular parison, if desired.

In this invention, bags 10, 12 contain an opaque, relatively rigid, hollow sealing member 18, 20. Each of sealing members 18, 20 are of the general shape of a truncated cone, and are open at both ends to define a tapering bore 22 therethrough.

Hollow sealing members 18, 20 are proportioned to nest with each other, as shown at FIGS. 2 and 3, with portion 24 of the walls of bags 10, 12 positioned therebetween. As can be seen from FIG. 2, a portion 26 of the wall portions 24 is accordingly positioned to block fluid flow through the bores 22 of the hollow, nested, conical sealing members 18, 20.

Also, it can be seen that any contamination 28 on the outside of the bag walls 10, 12 is sealed in the interface 30 between the respective wall sections 24 positioned between conical sealing members 18, 20.

Conical sealing members 18, 20 may advantageously be made out of dark anodized aluminum, or another metal which is capable of absorbing the particular radiation used in the irradiation step. Accordingly, as the next step, the nested conical sealing members are exposed to irradiation as in FIG. 3, for example by focused infrared lamps providing radiation 32, 34 from two or more directions.

The irradiation can be provided to the system by any means, such as visible, infrared, ultraviolet, or radio frequency radiation as may be desired. The term "opaque" implies the capability to absorb a high percentage of the particular radiant energy to which it is exposed. The term "transparent" implies that a lower percentage of the radiant energy as applied is absorbed.

Lasers may also be used as desired to provide the radiant energy, while microwave energy or the like may be particularly desirable for use with metal conical sealing members as specifically suggested above.

During the exposure to radiation 32, 34, the nested sealing members 18, 20 are heated, with the result that heat is conducted to the portions 24 of the transparent walls between the nested sealing members 18, 20 to a temperature sufficient to seal the transparent walls together, which temperature, of course, conventionally varies depending upon the particular thermoplastic material used. The overall sealing temperature will be controlled by the intensity and duration of radiation 32, 34.

At least one of sealing members 18, 20, and preferably both of them, may define an annular, tear line-forming ridge 36, positioned on either the inner or outer side surfaces of conical members 18, 20 with the nested conical members being positioned so that one of the tear line-forming ridges 36 presses an annular portion of wall segment 24 against the other sealing member. Accordingly, during the irradiation step, while most of wall segment 24 may be sealed together by the heating action of the pair of nested sealing members 18, 20, tear line forming ridge 36 will dig into the heated plastic to form the line of tearing weakness 37, preferably positioned intermediate the ends of the sealed area 24, to permit severing about the annular line of weakness 37 and removal of the portion 26 that blocks flow through bores 22 of the conical sealing members 18, 20.

As a result of this, section 26, comprising segments of walls 10, 12, and sealed at its periphery 38, may be removed from flow-blocking relationship with the nested sealing members 18, 20.

Severed and sealed portion 26 of wall 10, 12, containing non-sterile surfaces well sealed within the interior of the sealed section, may then be removed from its flow blocking relation with bores 22 by pressurizing container 10 with air or liquid as may be desired, relative to container 12, to create a pressure imbalance indicated by arrow 40, to complete the severing and removing action which was begun by ridge 36. Segment 26 then simply falls into bag 12 and remains there, opening a preferably sterile, sealed passageway between containers 10 and 12.

Alternatively, the wall of bag 12 may define a molded pull tab or projection 42, as shown in FIG. 3. After the sealing step is complete so that section 24 of the bag wall has been sealed, it is possible from outside of the bag, by manual manipulation, to grasp member 42 through the flexible walls of the bag and to pull it, severing sealed segment 26a about the tear line formed by ridge 36 in a manner similar to the embodiment shown in FIG. 2, causing the removal of segment 26a and the opening of bores 22 of the nested sealing members 18, 20, for opening of a sterile path between the two containers 10, 12.

Alternatively, conical sealing members 18, 20 may be made of a preferably carbon-filled, high melting plastic material, for example, polycarbonate plastic or polytetrafluoroethylene. In this instance, tear line forming ridge 36 may advantageously be a metal ridge insert in menbers 18, 20, which is capable of absorbing and focusing an increased amount of energy for weakening segment 24 at the desired spot.

Optional flanges 44 are provided on members 18, 20 to facilitate the manual manipulation thereof within the bag by the user, and to support the bag walls.

It is particularly desirable for each of the conical sealing members 18, 20 to define an annular ridge 36 for forming a line of tearing weakness in the operation, even though one of them will not be used in a specific operation. However, the presence of the extra seal line 36 facilitates the continued joining of containers together. By the system of this invention, an indefinite number of containers can be joined together, simply by adding another container having a conical sealing member similar to members 18, 20, where the container may be brought together against either container 10 or 12, and the sealing member nested into position with the nested, already-used sealing members 18, 20. The sealing members 18, 20 may be stacked one after another for multiple sterile connections. This has the advantage of closing off the intermediate bags and providing a flow channel passing through all of the bags, from one end bag of the series of connections to the newly added bag, should that be desired.

Alternatively, just one of members 18, 20 may be used if the other sealing member has been removed. For example, one of the sealing members 18, 20 may be removed from the seal which is formed and brought to the other side of its bag, or another portion of the bag surface, where another connection may be made with another bag containing a separate sealing member.

Accordingly, the invention of this application provides a sterile connection to a flexible, thermoplastic container in which the outer wall portions of the container are breached through in accordance with this invention, but the non-sterile outer surfaces are sealed so that only inner portions of the bag wall are exposed to the bag interior.

If desired, this invention may be used with containers which have relatively rigid portions, with only a segment of the container comprising the transparent, flexible, thermoplastic sealed wall. Also, as stated above, any number of bags in accordance with this invention may be connected together, either in a linear connection by nesting the various conical sealing members together, or by forming separate and branching sterile connections on the various bags. In fact, many types of flexible, thermoplastic walled containers may take advantage of the invention of this application, simply by the insertion of one or more sealing members 10, 12 in accordance with this invention into the bag, followed by sealing and sterilization, where such is desired.

The above has been offered for illustrative purposes only, and is not intended to limit the invention of this application, which is as defined in the claims below.

That which is claimed is:

1. A method of providing sealed, sterile connection between a pair of containers having transparent, flexible, thermoplastic, sealed walls, each of which contains an opaque, relatively rigid, hollow sealing member in the general shape of a truncated cone, open at both ends, which method comprises:
bringing said containers together into facing contact; nesting said hollow sealing members together with portions of said transparent walls of said containers positioned therebetween, being positioned to block fluid flow through said hollow nested sealing members; and irradiating said nested sealing members through at least one transparent container wall to heat said nested sealing members, whereby heat is conducted to said portions of the transparent walls between said nested sealing members to seal said transparent walls together; severing an annular portion of the sealed transparent walls in such a manner as to avoid exposure of said containers to the exterior; and removing from the nested sealing members the portion of the transparent walls which blocks fluid flow through said hollow, nested sealing members.

2. The method of claim 1 in which a plurality of sources of irradiation are used to simultaneously irradiate said nested sealing members from a plurality of directions.

3. The method of claim 1 in which said sealing members define means for forming an annular tear line to permit severing said portions within the sealed portion of the transparent walls in a manner to cause said containers to remain sealed from the exterior.

4. The method of claim 3 in which said annular tear line is severed by manual pulling of the portion of transparent walls which blocks fluid flow through the hollow nested sealing members out of engagement with the nested sealing members.

5. The method of claim 3 in which said weakened portion is severed by pressurizing one of the containers relative to the other, whereby the portion of the attached transparent walls which blocks fluid flow through said hollow nested cones is torn free along said tear line and pushed out of said nested cones.

6. The method of claim 3 in which said conical sealing members are made of metal.

7. The method of claim 3 in which said conical sealing members are made of a relatively high melting plastic.

8. A method of providing sealed, sterile connection between a pair of containers having transparent, flexible, thermoplastic, sealed walls, each of which contains an opaque, relatively rigid, hollow sealing member in the general shape of a truncated cone, open at both ends, and defining annular ridge means on at least one surface thereof, which method comprises:
bringing said containers together into facing contact; nesting said hollow sealing members together with portions of said transparent walls of said containers positioned therebetween and positioned to block fluid flow through hollow, nested cones; and irradiating said nested sealing members through said transparent container walls to heat said nested sealing members, whereby heat is conducted to said portions of the transparent walls between said nested, sealing members to seal the portions of said transparent walls together in at least one annular seal area; forming by said ridge means an annular line of tearing weakness in said sealed, annular area, and severing said annular seal into two annular sections and removing from said nested sealing members the annular section having the attached, transparent walls which block fluid flow through said hollow, nested cones.

9. A container comprising a transparent, flexible thermoplastic, sealed wall, said container carrying therein an opaque, relatively rigid, hollow sealing member in the general shape of a truncated cone, open at both ends, said sealing member defining about its side annular ridge means for impressing an annular tear line into said container wall upon heating, whereby said container may be brought together with an identical container, and said hollow sealing members may be nested together with portions of the transparent walls of the containers positioned therebetween, and said containers may be irradiated to heat the nested, sealing members to conduct heat to portions of the transparent walls between said nested sealing members to seal the transparent walls and to form said annular tear line within said seal, to permit opening of a sealed sterile flow path between the containers.

10. The container of claim 9 which defines a projection attached to said flexible wall, and adapted to project outwardly through an open end of the nested sealing members when the containers are in said nested position, whereby, after sealing, the portion of the sealed container walls may be manually removed from flow-blocking relation with said hollow, nested sealing members from outside of the container.

11. The container of claim 9, in which said hollow sealing member defines said annular ridge means on its inner surface.

12. The container of claim 9 in which said conical sealing member is made of metal.

13. The container of claim 9 which is made of a high-melting plastic, said annular ridge means defining a metal insert therein.

14. A sealed connection between a pair of containers having transparent, flexible, thermoplastic, sealed walls, each of which containers contains an opaque, relatively rigid, hollow sealing member in the general shape of a truncated cone, open at both ends, and defining annular tear line forming means on at least one surface thereof, said truncated cone sealing members being positioned together in nesting contact with portions of the transparent walls of said containers positioned therebetween, and at least one annular seal between the transparent walls of said containers positioned between the sealing members, and a line of tearing weakness in said seal formed by said tear line forming means, whereby the section of said transparent walls which blocks fluid flow through said hollow, nested cones may be torn away and removed for communication between the respective containers, while said annular seal prevents communication of said containers with the exterior.

15. The sealed connection of claim 14 in which said sealing members are made of metal.

16. The sealed connection of claim 14 in which said sealing members are made of a high melting plastic.

17. A container comprising a transparent, flexible, thermoplastic, sealed wall, said container carrying therein an opaque, relatively rigid, apertured sealing member, whereby said container may be brought together with an identical container, and the respective apertured sealing members may be brought into facing, abutting relation with registering apertures and with portions of the transparent walls of the container positioned therebetween, and said container may be irradiated to heat the abutting, sealing members to conduct heat to portions of the transparent walls between the sealing members to seal the transparent walls of said containers together, and means permitting severing of said container walls in the sealed portion to permit opening of a sealed, sterile flow path between the containers through said apertures.

18. A method of providing sealed connection between a pair of containers having transparent, flexible thermoplastic, sealed walls, each of which contains an opaque, relatively rigid apertured sealing member, which method comprises:

bringing said containers together into facing contact, abutting said hollow sealing members together with their apertures in registry and with portions of said transparent walls of said containers positioned therebetween, and irradiating said abutting sealing members through at least one transparent container wall to heat said abutting sealing members, whereby heat is conducted to said portions of the transparent walls between said abutting sealing members to seal said transparent walls together; and severing said sealed transparent walls in such a manner as to avoid exposure of said container interiors to the exterior surfaces of said walls, to open a fluid flow path through said registering apertures of the sealing members.

* * * * *